United States Patent
Liang et al.

(10) Patent No.: US 10,702,856 B2
(45) Date of Patent: Jul. 7, 2020

(54) CATALYSTS MADE WITH MANGANESE TUNGSTEN OXIDE FOR THE OXIDATIVE COUPLING OF METHANE

(71) Applicant: SABIC Global Technologies B.V., Bergen op Zoom (NL)

(72) Inventors: Wugeng Liang, Sugar Land, TX (US); Sagar Sarsani, Sugar Land, TX (US); David West, Sugar Land, TX (US)

(73) Assignee: SABIC GLOBAL TECHNOLOGIES B.V., Bergen op Zoom (NL)

( * ) Notice: Subject to any disclaimer, the term of this patent is extended or adjusted under 35 U.S.C. 154(b) by 0 days.

(21) Appl. No.: 16/303,278

(22) PCT Filed: May 16, 2017

(86) PCT No.: PCT/IB2017/052885
§ 371 (c)(1),
(2) Date: Nov. 20, 2018

(87) PCT Pub. No.: WO2017/208099
PCT Pub. Date: Dec. 7, 2017

(65) Prior Publication Data
US 2019/0210006 A1   Jul. 11, 2019

Related U.S. Application Data

(60) Provisional application No. 62/343,381, filed on May 31, 2016.

(51) Int. Cl.
 *B01J 23/34*   (2006.01)
 *C07C 2/84*   (2006.01)
 (Continued)

(52) U.S. Cl.
 CPC ............... *B01J 23/34* (2013.01); *B01J 21/08* (2013.01); *B01J 23/002* (2013.01); *B01J 23/04* (2013.01);
 (Continued)

(58) Field of Classification Search
 CPC . B01J 23/34; B01J 21/08; B01J 23/002; B01J 23/04; B01J 37/04; B01J 37/08;
 (Continued)

(56) References Cited

U.S. PATENT DOCUMENTS

| 3,526,645 A | * | 9/1970 | Wolpers | ............... | C07D 301/19 |
| | | | | | 549/529 |
| 8,129,305 B2 | * | 3/2012 | Bagherzadeh | ......... | B01J 23/002 |
| | | | | | 502/241 |

(Continued)

FOREIGN PATENT DOCUMENTS

| WO | WO 2011/149996 | 12/2011 |
| WO | WO 2013/082318 | 6/2013 |

(Continued)

OTHER PUBLICATIONS

A. Malekzadeh et al., "Oxidative Coupling of Methane over Lithium Doped (Mn+W)/SiO2 Catalysts." Journal of Natural Gas Chemistry 16, pp. 121-129. (Year: 2007).*

(Continued)

*Primary Examiner* — Patricia L. Hailey
(74) *Attorney, Agent, or Firm* — Norton Rose Fulbright US LLP

(57) ABSTRACT

Disclosed is a supported catalyst and methods to prepare and use the supported catalyst in an oxidative coupling of methane (OCM) reaction. The supported catalyst can contain $MnWO_4$ or $MnWO_4$ nanostructures that are in contact with the surface of a sodium containing silicon dioxide (Continued)

support material. The supported $MnWO_4$ catalyst can have an active $MnWO_4$ crystal phase.

20 Claims, 3 Drawing Sheets

(51) Int. Cl.

| | | |
|---|---|---|
| *B01J 37/04* | (2006.01) | |
| *B01J 37/08* | (2006.01) | |
| *B01J 23/00* | (2006.01) | |
| *B01J 21/08* | (2006.01) | |
| *B01J 23/04* | (2006.01) | |
| *C07C 11/04* | (2006.01) | |
| *C07C 27/14* | (2006.01) | |
| *C07C 29/48* | (2006.01) | |
| *C07C 31/08* | (2006.01) | |
| *B01J 37/02* | (2006.01) | |
| *B01J 35/00* | (2006.01) | |

(52) U.S. Cl.
CPC ............... *B01J 37/04* (2013.01); *B01J 37/08* (2013.01); *C07C 2/84* (2013.01); *C07C 11/04* (2013.01); *C07C 27/14* (2013.01); *C07C 29/48* (2013.01); *C07C 31/08* (2013.01); *B01J 35/0013* (2013.01); *B01J 37/0236* (2013.01); *B01J 2523/00* (2013.01); *B01J 2523/12* (2013.01); *B01J 2523/69* (2013.01); *B01J 2523/72* (2013.01); *C07C 2523/30* (2013.01); *C07C 2523/34* (2013.01); *Y02P 20/52* (2015.11)

(58) Field of Classification Search
CPC .................................................. B01J 35/0013; B01J 37/0236; B01J 2523/00; B01J 2523/12; B01J 2523/69; B01J 2523/72; C07C 2/84; C07C 11/04; C07C 27/14; C07C 29/48; C07C 31/08; C07C 2523/30; C07C 2523/34; Y02P 20/52
USPC .......................... 502/243, 254, 317, 324, 344
See application file for complete search history.

(56) References Cited

U.S. PATENT DOCUMENTS

| | | | |
|---|---|---|---|
| 2013/0165728 A1 | 6/2013 | Zurcher et al. | |
| 2013/0178664 A1* | 7/2013 | Zhou ................... | B01J 37/0244 568/885 |
| 2014/0107385 A1 | 4/2014 | Schammel et al. | |
| 2016/0122261 A1 | 5/2016 | Schammel et al. | |
| 2016/0297781 A1* | 10/2016 | Zakzeski ................ | B01J 27/047 |
| 2018/0311658 A1* | 11/2018 | Liang ..................... | B01J 37/033 |

FOREIGN PATENT DOCUMENTS

| | | | |
|---|---|---|---|
| WO | WO 2013/177461 | 11/2013 | |
| WO | WO-2017208099 A1 * | 12/2017 | ............. B01J 21/08 |

OTHER PUBLICATIONS

Arndt et al., "Mn—$Na_2WO_4$/$SiO_2$ as catalysts for the oxidative coupling of methane. What is really known?" *Applied Catalysis A: General*, 2012, 425-426:53-61.

Chua et al., "Oxidative coupling of methane for the production of ethylene over sodium-tungsten-manganese-supported-silica catalyst (Na—W—Mn/$SiO_2$)" *Applied Catalysis A: General*, 2008, 343:142-148.

Dedov et al., "Oxidative coupling of methane to form ethylene: effect of the preparation method on the phase composition and catalytic properties of Li—W—Mn—O—$SiO_2$ composite materials," *Petroleum Chemistry*, 2015, 55(2):163-168.

Fang et al., "Oxidative Coupling of Methane on Tungsten Manganese Catalysts" *Journal of Molecular Catalysis (China)*, 1992, 6:427-433 (English Abstract).

Fang et al., "Preparation and Characterization of Tungsten Manganese Catalyst for Oxidative Coupling of Methane" *Journal of Molecular Catalysis (China)*, 1992, 6:255-262 (English translation not available).

Hiyoshi et al., "Oxidative coupling of methane over alkali chloride-Mn—$Na_2WO_4$/$SiO_2$ catalysts: Promoting effect of molten alkali chloride," *Fuel Processing Technology*, 2015, 133:29-34.

International Search Report and Written Opinion issued in International Patent Application No. PCT/IB2017/052885, dated Aug. 10, 2017.

Ji et al., "Role of sodium in the oxidative coupling of methane over Na—W—Mn/$SiO_2$ catalysts," *Journal of Natural Gas Chemistry*, 1999, 8(1):1-8.

Ji et al., "Study on methane activation over Na—W—Mn/$SiO_2$ catalysts. Structure of the active center," *Fenzi Cuihua*, 2000, 14(1):1-5 (English Abstract).

Nipan, G.D., "Phase states of Na/W/Mn/$SiO_2$ Composites at temperature of catalytic oxidative coupling of methane," *Inorganic Materials*, 2014, 50(10):1012-1017.

Wang et al., "Comparative study on oxidation of methane to ethane and ethylene over $Na_2WO_4$—Mn/$SiO_2$ catalysts prepared by different methods." *Journal of Molecular Catalysis A: Chemical*, 2006, 245:272-277.

Wu et al., "Performance of $Mn_2O_3$—$Na_2WO_4$/$SiO_2$ catalyst doped with alkali chloride in oxidative coupling of methane," *Fenzi Cuihua*, 1994, 6(2):131-137. (English Abstract).

Yildiz et al., "Enhanced catalytic performance of $Mn_xO_y$—$Na_2WO_4$/$SiO_2$ for the oxidative coupling of methane using an ordered mesoporous silica support," *Chem. Commun.*, 2014, 50:14440-14442.

* cited by examiner ured catalyst of the present invention, preferably a nanostructured MnWO$_4$ supported catalyst, with sodium in the support material, can have equal to or higher methane (CH$_4$) conversion, oxygen (O$_2$) conversion, and C$_2$+ selectivity when compared with conventional OCM catalysts. The supported catalysts of the present invention can be obtained by adding an effective amount of sodium to produce a sodium containing SiO$_2$ material. Without being bound by theory, it is believed that adding sodium to the support material bonds the sodium to the silica and transforms the silica to the desired phase during calcination. The support material can be then combined with MnWO$_4$ or MnWO$_4$ nanostructures in an aqueous mixture, dried, and then calcined to produce the supported catalysts of the present invention. Supported catalysts prepared in this manner can catalyze the OCM reaction and achieve higher CH$_4$ and O$_2$ conversion and higher C$_2$+ hydrocarbon selectivity when compared with conventional OCM catalysts.

CATALYSTS MADE WITH MANGANESE TUNGSTEN OXIDE FOR THE OXIDATIVE COUPLING OF METHANE

CROSS REFERENCE TO RELATED APPLICATIONS

This application is a national phase application under 35 U.S.C. § 371 of International Application No. PCT/IB2017/052885 filed May 16, 2017, which claims the benefit of priority of U.S. Provisional Patent Application No. 62/343,381 filed May 31, 2016. The entire contents of each of the above-referenced disclosures are specifically incorporated herein by reference without disclaimer.

BACKGROUND OF THE INVENTION

A. Field of the Invention

The invention generally concerns a supported catalyst and methods to prepare and use the supported catalyst in an oxidative coupling of methane (OCM) reaction. The supported catalyst can include a silicon dioxide (SiO$_2$) support material that includes sodium (Na) and manganese tungsten tetroxide (MnWO$_4$) in contact with the SiO$_2$ support material.

B. Description of Related Art

Ethylene is the world's largest commodity chemical and the chemical industry's fundamental building block. For example, ethylene derivatives can be found in food packaging, eyeglasses, cars, medical devices, lubricants, engine coolants, and liquid crystal displays. For industrial scale applications, ethylene commercial production can involve heating natural gas condensates and petroleum distillates, which include ethane and higher hydrocarbons. The produced ethylene can be separated from the product mixture using gas separation processes. FIG. 1 provides an example of products generated from ethylene.

Ethylene and other C$_2$+ hydrocarbon products can also be produced from methane through the oxidative coupling of methane (OCM) reaction. Over the past 40 years since the first reported OCM reaction, many methane activation catalysts have been developed. Among these catalysts, Mn—Na$_2$WO$_4$ supported on silicon dioxide (SiO$_2$) has been used in the OCM reaction. See X. P. Fang, et al., (*Journal of Molecular Catalysis* (China), 1992, Vol. 6, pp. 255-262), and Arndt, S., et al., (*Applied Catalysis A: General*, 2012, Vols. 425-426, pp. 53-61). Other OCM catalysts include MnWO$_4$ nanowires mixed with a silica support material. By way of example, International Application Publication No. WO2013177461 to Cizeron et al. and U.S. Application Publication No. 20130165728 to Zurcher et al. each describe using MnWO$_4$ nanowires made from a biological template on various metal oxide supports. These catalysts require several complicated processing steps that undermine the efficiency of the production process, and ultimately the scalability and commercial viability of the resulting catalyst. Even further, these catalysts made from biological templates have relatively poor catalytic performance when compared with other known OCM catalysts.

While there have been various attempts to produce catalysts for the OCM reaction, such catalysts still suffer from low performance, operational inefficiencies, catalyst deactivation (e.g., sintering and coking at high temperatures), and costly preparation methods.

SUMMARY OF THE INVENTION

A solution to the problems associated with catalysts used in the OCM reaction has been discovered. The solution resides in connecting MnWO$_4$ to the surface of a silicon dioxide support material that contains sodium. Such a connection provides a supported catalyst having an active MnWO$_4$ crystal phase. Notably, and in one non-limiting embodiment, the manganese and tungsten are not isolated islands in the support material. It is believed that by having the manganese and tungsten connected together (e.g., an active crystal MnWO$_4$ phase), enhanced conversion and selectivity parameters can be achieved. By way of example, a MnWO$_4$ supp In a particular aspect of the invention, there is disclosed a supported MnWO$_4$ catalyst including a silicon dioxide (SiO$_2$) support material containing sodium (Na) and manganese tungsten tetroxide (MnWO$_4$) in contact with the SiO$_2$ support material. The molar ratio of Mn to W in the supported MnWO$_4$ catalyst can be 1:1. The supported catalyst can contain a MnWO$_4$ crystal phase. In another aspect, the MnWO$_4$ catalytic material can be in the form of nanostructures that have at least one dimension of 1 nm to 1000 nm, 25 to 500 nm, or 30 nm to 200 nm. In some aspects, the MnWO$_4$ nanostructures can be nanowires, nanoparticles, nanorods, nanotubes, nanocubes, or a combination thereof. In particular, the MnWO$_4$ nanostructures can be nanorods having a diameter of 10 to 50 nm and/or a length of 150 nm to 250 nm. In one non-limiting aspect of the present invention, a distinguishing feature of the supported catalysts of current invention is that they can be devoid of a Na$_2$WO$_4$ crystal phase and devoid of a MnMn$_6$SiO$_{12}$ crystal phase. Another non-limiting distinguishing feature is that the MnWO$_4$ nanostructures can be grafted to the surface of the support material rather than impregnated in the pores of this support material.

Also disclosed is a method for preparing the supported MnWO$_4$ catalyst of the present invention. The method can include: (a) obtaining an aqueous mixture comprising manganese tungsten oxide (MnWO$_4$) and a silica support material that includes sodium; (b) drying the mixture to obtain a crystalline material; and (c) calcining the crystalline material to obtain a MnWO$_4$ supported catalyst. In one aspect, the silica support material in step (a) can be obtained by: (i) obtaining an aqueous mixture of a sodium source and silica sol; (ii) drying the mixture to obtain a crystalline material; and (iii) calcining the crystalline material to obtain the silica support material. The sodium source can be NaCl, NaNO$_3$, Na$_2$CO$_3$, Na$_2$O, or a mixture thereof, preferably NaCl. In step (b), the mixture of step (a) can be dried by subjecting the mixture to a temperature of 110° C. to 130° C. for 1 hours to 15 hours, preferably about 125° C. Calcining in step (c) can include subjecting the crystalline material to a temperature of 350° C. to 800° C., preferably about 500° C. in the presence of air. The disclosed method provides a $MnWO_4$ supported catalyst that has a $MnWO_4$ phase in the crystal structure.

The supported catalysts of the current invention are also capable of catalyzing an oxidative coupling of methane reaction. A method for producing $C_2$+ hydrocarbons from the oxidative coupling of methane reaction is described. The method can involve contacting a reactant feed that includes methane ($CH_4$) and oxygen ($O_2$) with a supported catalyst of the present invention under reaction conditions sufficient to produce a product stream that includes $C_2$+ hydrocarbons. Notably, the catalyst of the present invention has an improved performance as compared to conventional OCM catalysts. For the OCM reaction, in addition to activity and selectivity, another indicator for the performance of a catalysts used is the sum of $CH_4$ conversion and $C_2$+ hydrocarbon selectivity. While previously used catalysts typically provided a sum of $CH_4$ conversion and $C_2$+ hydrocarbon selectivity of less than 100, the catalysts of the present invention can achieve a sum that is greater than 100.

The term "catalyst" means a substance which alters the rate of a chemical reaction. "Catalytic" means having the properties of a catalyst.

The term "conversion" means the mole fraction (i.e., percent) of a reactant converted to a product or products.

The term "selectivity" refers to the percent of converted reactant that went to a specified product, e.g., $C_2$+ hydrocarbon selectivity is the % of methane that formed ethane, ethylene and higher hydrocarbons.

The phrase "in contact with" in the context of the present invention means dispersed on the surface of the support material or inside the support material or connected to support material through covalent bonding, ionic bonding, Van der Waals interaction, or other interactions. A non-limiting example of in contact with is the interaction of $MnWO_4$ with the sodium containing silicon dioxide support material.

The term "graft" or "grafted" refers to the interaction or bonding of the oxygen of the support material with the catalytic material. A non-limiting example is the Si—O—Mn—W or Si—O—W—Mn interaction or bonding of the catalysts of the present invention.

"Nanostructure" means a structure having at least one diameter on the order of nanometers (e.g. between about 1 and 1000 nanometers, preferably 25 to 500 nm, or more preferably 30 nm to 200 nm). A nanostructure can be nanowires, nanoparticles, nanorods, nanotubes, or nanocubes. A "nanowire" means a nanowire structure having at least one diameter on the order of nanometers (e.g. between about 1 and 1000 nanometers, preferably 25 to 500 nm, or more preferably 30 nm to 200 nm) and an aspect ratio greater than 1:1, preferably greater than 5:1, or more preferably greater than 10:1. The "aspect ratio" of a nanowire is the ratio of the actual length (L) of the nanowire to the diameter (D) of the nanowire.

The terms "about" or "approximately" are defined as being close to as understood by one of ordinary skill in the art. In one non-limiting embodiment, the terms are defined to be within 10%, preferably within 5%, more preferably within 1%, and most preferably within 0.5%.

The term "substantially" and its variations are defined to include ranges within 10%, within 5%, within 1%, or within 0.5%.

The terms "inhibiting" or "reducing" or "preventing" or "avoiding" or any variation of these terms, when used in the claims and/or the specification includes any measurable decrease or complete inhibition to achieve a desired result.

The term "effective," as that term is used in the specification and/or claims, means adequate to accomplish a desired, expected, or intended result.

The use of the words "a" or "an" when used in conjunction with any of the terms "comprising," "including," "containing," or "having" in the claims, or the specification, may mean "one," but it is also consistent with the meaning of "one or more," "at least one," and "one or more than one."

The terms "wt. %", "vol. %", or "mol. %" refers to a weight, volume, or molar percentage of a component, respectively, based on the total weight, the total volume of material, or total moles, that includes the component. In a non-limiting example, 10 grams of component in 100 grams of the material is 10 wt. % of component.

The words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The catalysts of the present invention can "comprise," "consist essentially of," or "consist of" particular ingredients, components, compositions, etc. disclosed throughout the specification. With respect to the transitional phase "consisting essentially of," in one non-limiting aspect, a basic and novel characteristic of the catalysts of the present invention is their capability to catalyze the production of $C_2$+ hydrocarbons from a gas that contains methane.

Other objects, features and advantages of the present invention will become apparent from the following figures, detailed description, and examples. It should be understood, however, that the figures, detailed description, and examples, while indicating specific embodiments of the invention, are given by way of illustration only and are not meant to be limiting. Additionally, it is contemplated that changes and modifications within the spirit and scope of the invention will become apparent to those skilled in the art from this detailed description.

DETAILED DESCRIPTION OF THE INVENTION

Figure 1:
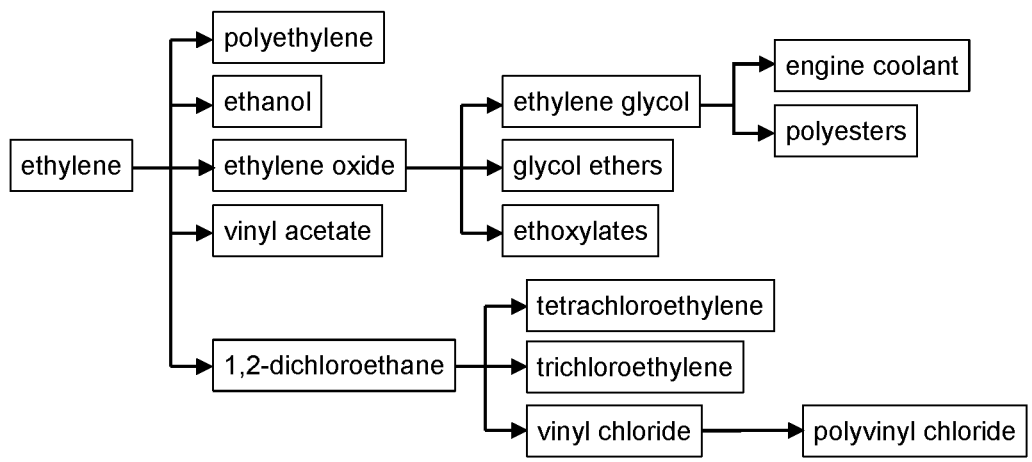
FIG. 1 depicts an illustration of various chemicals and products that can be produced from ethylene.

Currently available processes to produce light olefins (e.g., ethylene) by OCM are often thwarted by low performance, catalyst agglomeration, and sintering. This leads to $CH_4$ conversion and $C_2$+ hydrocarbon selectivity limits that make commercial operation impractical or unfeasible. A discovery has been made that includes an OCM catalyst where $MnWO_4$ or $MnWO_4$ nanostructures are in contact with the surface (e.g., grafted to) of a sodium containing silicon dioxide support material. Such a catalyst can have improved methane ($CH_4$) conversion, improved oxygen ($O_2$) conversion, and improved $C_2+$ selectivity when compared with conventional OCM catalysts. Further, the catalysts of the present invention can have a sum of the percentages of $CH_4$ conversion and $C_2+$ hydrocarbon selectivity of greater than 100.

These and other non-limiting aspects of the present invention are discussed in further detail in the following sections.

A. Supported $MnWO_4$ Catalyst

The supported $MnWO_4$ catalysts of the present invention can include catalytic $MnWO_4$ material (e.g., nanostructures) and a support material. The $MnWO_4$ or $MnWO_4$ nanostructures can be connected to a silicon dioxide support material that includes an effective amount of sodium to inhibit coking of the catalyst and/or sintering of the metals at high temperatures and/or pressures.

1. $MnWO_4$ Material

The catalytic material can include manganese tungsten oxides. Non-limiting examples of the manganese tungsten oxide include powdered manganese tungsten tetraoxide ($MnWO_4$) having varying mesh sizes, including nanosized $MnWO_4$ particles or structures, or combinations thereof. In a particular aspect, the $MnWO_4$ can be $MnWO_4$ nanostructures having at least one, at least two, or all three dimensions of 1 nm to 1000 nm, 25 to 500 nm, or 30 nm to 200 nm and all ranges there between including 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, or 199 nm. The $MnWO_4$ nanostructures can be nanowires, nanoparticles, nanorods, nanotubes, nanocubes, or combinations thereof. In a preferred aspect, the catalytic material is $MnWO_4$ nanorods having a diameter of 10 to 50 nm and all diameters there between including 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, or 49 nm and/or a length of 150 nm to 250 nm and all lengths there between including 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, or 249 nm. In a non-limiting embodiment, commercially available $MnWO_4$ nanorods are available from Novarials Corporation (Woburn, Mass., USA).

The amount of catalytic material in the catalyst depends, inter alia, on the desired catalytic activity of the catalyst. In some embodiments, the amount of catalytic material present in the catalyst ranges from 1 to 100 parts by weight of catalytic material per 100 parts by total weight of catalyst or from 10 to 50 parts by weight of catalytic material per 100 parts by weight of total catalyst. In specific embodiments, the amount of catalytic material present ranges from 5 to 20 parts by weight of catalytic material per 100 parts by weight of catalyst and all parts by weight there between including 6, 7, 8, 9, 10, 11, 12, 13, 14, 15, 16, 17, 18, and 19 parts by weight (wt. %).

2. $SiO_2$ Support Material

The support material or a carrier can be porous and have a high surface area. In some embodiments, the support can include an inorganic oxide, silicon dioxide ($SiO_2$), alpha, beta or theta alumina ($Al_2O_3$), activated $Al_2O_3$, titanium dioxide ($TiO_2$), magnesium oxide (MgO), calcium oxide (CaO), strontium oxide (SrO), zirconium oxide ($ZrO_2$), zinc oxide (ZnO), lithium aluminum oxide ($LiAlO_2$), magnesium aluminum oxide ($MgAlO_4$), manganese oxides (MnO, $MnO_2$, $Mn_2O_4$), lanthanum oxide ($La_2O_3$), activated carbon, silica gel, zeolites, activated clays, silicon carbide (SiC), diatomaceous earth, magnesia, aluminosilicate, calcium aluminate, or combinations thereof. In a specific embodiment, the support can include water insoluble, amorphous $SiO_2$ suspended in aqueous solution by colloid distribution, such as the $SiO_2$ found in silica sol. Commercially available silica sol (BEVASIL® 30 or Levasil® 200/30% FG, AzkoNobel, Sweden) is a transparent, slightly opalescent aqueous silicic acid solution containing 30% colloid silicon dioxide. Preferably, the silica sol has a 34% silica content, which is commercially available from Nalco Company (Naperville, Ill., USA).

The support material contains, or is doped with, an alkali metal salt or alkaline earth metal (i.e., Columns 1 or 2 of the Periodic Table) or salt thereof. Non-limiting examples of metals include sodium (Na), lithium (Li), potassium (K), cesium (Cs), magnesium (Mg), calcium (Ca), or barium (Ba), or any combination thereof. In specific embodiments, the support material contains, or is doped with sodium. Non-limiting examples of sodium sources are sodium chloride (NaCl), sodium nitrate ($NaNO_3$), sodium carbonate ($Na_2CO_3$), sodium oxide ($Na_2O$) or a mixture thereof. In one embodiment, the source of sodium is NaCl. In a specific embodiment, the support is $SiO_2$, specifically silica sol containing $Na^+$ in an effective catalytic amount and/or an amount effective to transform the silica to the desired phase during calcination. The amount of sodium is insufficient to form a sodium silicate ($Na_2(SiO_2)_nO$) material. The sodium containing support material can contain 0.1 to 5 parts by weight of Na, preferably 1 to 2 parts by weight Na, and all parts by weight Na there between including 1.05, 1.1, 1.15, 1.2, 1.25, 1.3, 1.35, 1.4, 1.45, 1.5, 1.55, 1.6, 1.65, 1.7, 1.75, 18, 1.85, 1.9, or 1.95 parts by weight Na based on the total weight of the support material.

3. Method to Make the Support Material

Figure 2:
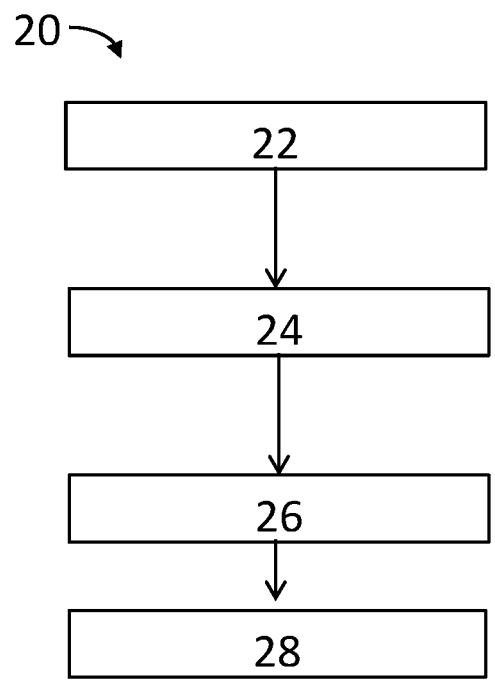
FIG. 2 is a schematic of a method of preparing the support material of the present invention.

Support materials may be prepared using generally known preparation techniques. Referring to FIG. 2 a schematic of the method 20 to prepare the support material is illustrated. In step 22, of method 20, the sodium source (e.g., NaCl) can be dissolved in water and added into a silica sol (e.g., a silica sol having a 34 wt. % silica content). In step 24, the resulting mixture can be mixed and dried. The drying of the aqueous mixture of a sodium source and silica sol can include subjecting the mixture to a temperature of 110, 111, 112, 113, 114, 115, 116, 117, 118, 119, 120, 121, 122, 123, 124, 125, 126, 127, 128, 120, or 130° C. for 1, 2, 3, 4, 5, 6, 7, 8, 9, 10, 11, 12, 13, 14, or 15 hours, preferably about 125° C. In step 26, the dried support material can be calcined. For example, the dried support material can be heated to a temperature of about 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, or 900° C.

for 1, 2, 3, 4, 5, 6, 7, 8, 9, 10, 11, 12, 13, 14, or 15 hours, preferably about 500 or about 800° C. for 5, 6, 7, or 8 hours in the presence of an oxygen source (e.g., air, oxygen, or oxygen enriched air) to afford the catalyst 28 of the present invention.

4. Methods of Making a $MnWO_4$ Catalyst

Figure 3:
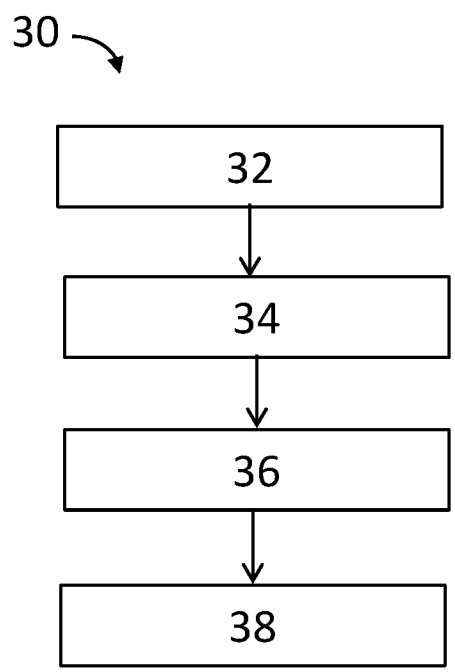
FIG. 3 is a flow diagram showing a method of preparing the supported catalyst in one embodiment of the present invention.

Referring to FIG. 3, an illustration of a method 30 for the preparation of the supported $MnWO_4$ catalyst is depicted. In step 32, the catalytic material (e.g., $MnWO_4$ or $MnWO_4$ nanostructures) and the sodium containing support material 28 may be mixed together using suitable mixing equipment. Examples of suitable mixing equipment include tumblers, stationary shells or troughs, Muller mixers (for example, batch type or continuous type), impact mixers, and any other generally known mixer, or generally known device, that can suitably provide the catalytic material/sodium containing support mixture. A magnetic stir bar can be used. In step 34, the $MnWO_4$ or $MnWO_4$ nanostructures/support material 28 mixture can be dried to obtain a crystalline material. Drying of the aqueous mixture of $MnWO_4$ or $MnWO_4$ nanostructures and a sodium containing silica support can include subjecting the $MnWO_4$ or $MnWO_4$ nanostructures/support material 28 mixture to a temperature of 110° C. to 130° C. for 1, 2, 3, 4, 5, 6, 7, 8, 9, 10, 11, 12, 13, 14, or 15 hours, preferably about 125° C. In step 36, the crystalline material can be calcined to obtain a $MnWO_4$ supported catalyst 38. Calcination of the dried crystalline material can include subjecting the crystalline material to a temperature of a 350° C. to 800° C. for 1 to 15 hours, preferably 450, 460, 470, 480, 490, 500, 510, 520, 530, 540, 550, 560, 570, 580, 590, 600, 625, 650, 675, 700, 725, 750, or 750° C. for 4, 5, 6, 7, or 8 hours in the presence of an oxygen source (e.g., air). When heating the solid $MnWO_4$ or $MnWO_4$ nanostructure to a high temperature (e.g., a calcination temperature), the $MnWO_4$ or $MnWO_4$ nanostructure can graft onto the surface of the sodium containing support material. In the $MnWO_4$ crystal phase the Mn and W can be chemically bound together or can be in close proximity with one another. Conventionally supported catalysts prepared with $Mn(NO_3)_2$ and $Na_2WO_4$ have $Na_2WO_4$ and $MnMn_6SiO_{12}$ crystal phases and do not form a $MnWO_4$ crystal phase where the Mn and W are chemically bound together or are in close proximity with one another.

B. Reactants

The reactant mixture in the context of the present invention can be a gaseous mixture that includes, but is not limited to, a hydrocarbon or mixtures of hydrocarbons and oxygen. The hydrocarbon or mixtures of hydrocarbons can include natural gas, liquefied petroleum gas containing of $C_2$-$C_5$ hydrocarbons, $C_6$+ heavy hydrocarbons (e.g., $C_6$ to $C_{24}$ hydrocarbons such as diesel fuel, jet fuel, gasoline, tars, kerosene, etc.), oxygenated hydrocarbons, and/or biodiesel, alcohols, or dimethyl ether, or combinations thereof. In a preferred aspect, the hydrocarbon is a mixture of hydrocarbons that is predominately methane (e.g., natural gas). The oxygen containing gas used in the present invention can be air, oxygen enriched air, or oxygen gas. The reactant mixture may further contain other gases, provided that these do not negatively affect the reaction. Examples of such other gases include carbon dioxide, nitrogen, and hydrogen. The hydrogen may be from various sources, including streams coming from other chemical processes, like ethane cracking, methanol synthesis, or conversion of methane to aromatics. Carbon dioxide can be obtained from natural gas or from a waste or recycle gas stream (e.g., from a plant on the same site, like for example from ammonia synthesis).

C. Oxidative Coupling of Methane Process

The reaction processing conditions can be varied as desired. In one non-limiting aspect, the reaction processing conditions can include contacting a feed stream comprising hydrocarbon(s) and oxidant(s) with any of the catalysts described throughout the specification under specifically selected OCM conditions (e.g., methane to oxygen ratio of 7.4 and a reaction temperature of 725° C.). This can result in a methane conversion of greater than 13.4% and a $C_2$+ selectivity greater than 75.5%. In one aspect of the present invention, the methane to oxygen ratio can be 7.4 and the reaction temperature can be about 800° C. where the methane conversion is 18% or more, 19% or more, and 20% or more. In another aspect, the $O_2$ conversion can be 98% or more, and preferably 99% or more. In another aspect the $C_2$+ selectivity can be 78% or more, 79% or more, and preferably 80% or more. In some preferred embodiments, the sum of the $CH_4$ conversion percentage and the $C_2$+ hydrocarbon selectivity percentage can be 100 or more. As described in more detail below, the methane to oxygen ratio, reaction temperature, and other processing parameters can be modified as desired.

In one aspect of the invention, the catalyst of the present invention can be used in continuous flow reactors to produce $C_2$+ hydrocarbons from methane (e.g., natural gas). Non-limiting examples of the configuration of the catalytic material in a continuous flow reactor are provided throughout this specification. The continuous flow reactor can be a fixed bed reactor, a stacked bed reactor, a fluidized bed reactor, or an ebullating bed reactor. In a preferred aspect of the invention, the reactor can be a fixed bed reactor. The catalytic material can be arranged in the continuous flow reactor in layers (e.g., catalytic beds) or mixed with the reactant stream (e.g., ebullating bed).

In certain embodiments, a volume of catalyst in the contacting zone of the continuous flow reactor can be in a range from about 10-60 vol. %, about 20-50 vol. %, or about 30-40 vol. % of a total volume of reactant in the contacting zone. Processing conditions in the continuous flow reactor may include, but are not limited to, temperature, pressure, oxidant source flow (e.g., air or oxygen), hydrocarbon gas flow (e.g., methane or natural gas), ratio of reactants, or combinations thereof. Process conditions can be controlled to produce $C_2$+ hydrocarbons with specific properties (e.g., percent ethylene, percent butene, percent butane, etc.). The average temperature in the continuous flow reactor can range from 600° C., 625° C., 650° C., 655° C., 660° C., 665° C., 670° C., 675° C., 680° C., 685° C., 690° C., 695° C., 700° C., 705° C., 710° C., 715° C., 720° C., 725° C., 730° C., 735° C., 740° C., 745° C., 750° C., 755° C., 760° C., 765° C., 770° C., 775° C., 780° C., 785° C., 790° C., 795° C., 800° C., 805° C., 810° C., 815° C., 820° C., 825° C., 830° C., 835° C., 840° C., 845° C., 850° C., 860° C., 870° C., 880° C., 890° C., 900° C., or any value or range there between. Pressure in the continuous flow reactor can range about 0.1 MPa to 2.0 MPa. The gas hourly space velocity (GHSV) of the reactant feed can range from 500 $h^{-1}$ to 100,000 $h^{-1}$ or more. In some embodiments, the GHSV can be as high as can be obtained under the reaction conditions. In some aspects of the present invention, the reactant mixture can have a molar ratio of methane to oxygen ranges from 0.3 to 20, 0.5 to 15, 1 to 10, or 5 to 7.5 or any range there between. The molar ratio of methane to oxygen can be 0.3, 0.5, 1, 1.5, 2, 2.5, 3, 3.5, 4, 4.5, 5, 5.5, 6, 6.5, 7, 7.5, 8, 8.5, 9, 9.5, 10, 15, or 20 or any value there between. Severity of the process conditions may be manipulated by changing the hydrocarbon source, oxygen source, pressure, flow rates, the temperature of the process, the catalyst type, and/or catalyst to feed ratio. In a preferred embodiment, the average temperature ranges from about 600° C. to about 900° C., and more preferably from about 700° C. to 800° C. or any range there between at 0.1 to 1.0 MPa and/or a GHSV from about from 500 to 50,000 h$^{-1}$ or more.

Figure 4:
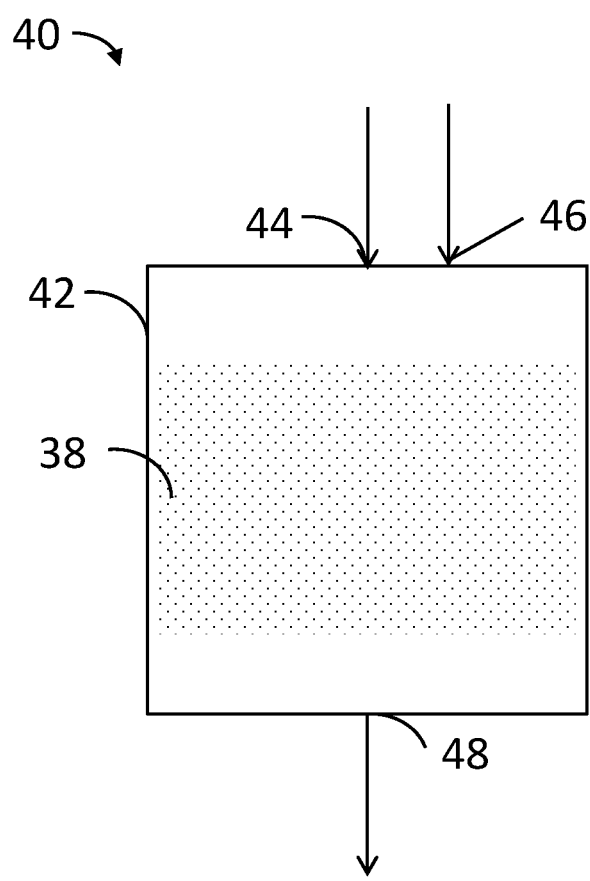
FIG. 4 is a schematic of a system of the present invention using the catalyst of the present invention in an oxidative coupling of methane reaction.

Referring to FIG. 4, a schematic of system 40 for the production of C$_2$+ hydrocarbons is depicted. System 40 can include a continuous flow reactor 42 and the supported MnWO$_4$ catalyst 38. A reactant stream that includes methane can enter the continuous flow reactor 42 via the feed inlet 44. An oxygen containing gas (oxidant) can be provided via oxidant source inlet 46. In some aspects of the invention, methane and the oxygen containing gas are fed to the reactor via one inlet. The reactants can be provided to the continuous flow reactor 42 such that the reactants mix in the reactor to form a reactant mixture prior to contacting the catalyst 38. In some embodiments, the catalytic material and the reactant feed can be heated to the approximately the same temperature. In some instances, the catalyst 38 may be layered in the continuous flow reactor 42. Contact of the reactant mixture with the catalyst 38 produces a product stream (for example, C$_2$+ hydrocarbons and generates heat (i.e., an exotherm or rise in temperature is observed). The product stream can exit continuous flow reactor 42 via product outlet 48.

The resulting product stream having C$_2$+ hydrocarbons can be separated using gas/liquid separation techniques (e.g., distillation, absorption, membrane technology, etc.) to produce gaseous streams that include carbon monoxide, carbon dioxide, hydrogen, C$_2$+ hydrocarbons product, and/or water. In a particular instance, the C$_2$+ hydrocarbons can be separated from hydrogen and carbon monoxide and/or carbon dioxide, if present, using gas/gas separation techniques (e.g., a hydrogen selective membrane, a carbon monoxide selective membrane, or cryogenic distillation) to produce streams of C$_2$+ hydrocarbons, carbon monoxide, carbon dioxide, hydrogen, or mixtures thereof. The resulting streams can be used in additional downstream reaction schemes to create additional products or for energy production. Examples of other products include chemical products such as methanol production, olefin synthesis (e.g., via Fischer-Tropsch reaction), aromatics production, carbonylation of methanol, carbonylation of olefins, the reduction of iron oxide in steel production, etc. The resulting streams can further be isolated and/or stored for later use. By way of example, FIG. 1 provides non-limiting examples of various chemicals that can be made from ethylene.

EXAMPLES

The present invention will be described in detail by way of specific examples. The following examples are offered for illustrative purposes only, and are not intended to limit the invention in any manner. Those of skill in the art will readily recognize a variety of noncritical parameters, which can be changed or modified to yield essentially the same results.

Example 1

Preparation of a Comparative Catalyst

The following comparative catalyst was made following the method of Wang J., et al., *Journal of Molecular Catalysis A: Chemical*, 2006, 245: 272-277.

Manganese nitrate hydrate (Mn(NO$_3$)$_2$.4H$_2$O, 1.74 g) was dissolved in water (15 mL) and the solution obtained was added into silica sol (34% silica content, 28.61 g). Sodium tungstate hydrate (Na$_2$WO$_4$.2H$_2$O, 1.12 g) was dissolved in water (10 mL) and the solution obtained was added to the above Mn/silica sol slurry. Additional water (50 mL) was added, and the resulting mixture was agitated at 90° C. for 2 hours. The resulting mixture was then dried overnight at 125° C. to remove the water, and calcined at 800° C. for 6 hours to obtain a catalyst ready for performance testing.

Example 2

Preparation of a Silicon Dioxide Support Containing Sodium

The silica support containing Na (Na—SiO$_2$) was prepared in the following manner. Sodium chloride (NaCl, 1.2 g) was dissolved in water (50 mL), and the solution obtained was added into silica sol (34% silica content, 82.26 g). The mixture obtained was then dried overnight at 125° C. and calcined at 800° C. for 6 hours.

Example 3

Preparation of a Catalyst of the Present Invention from Powdered MnWO$_4$

Support material (6.55 g) as prepared in Example 2 was mixed with powdered MnWO$_4$ (1.02 g) and water (15 mL). The slurry obtained was then dried overnight at 125° C. and calcined at 500° C. for 6 hours to obtain a comparative catalyst having microstructures of MnWO$_4$.

Example 4

Preparation of a Catalyst of the Present Invention from Nano MnWO$_4$

Support material (6.55 g) as prepared in Example 2 was mixed with MnWO$_4$ nanostructures (with 30 nm in diameter and 200 nm in length) (1.02 g, nanorods obtained from Novarials Corporation (Woburn, Mass., USA)) and water (15 mL). The slurry obtained was then dried overnight at 125° C. and calcined at 500° C. for 6 hours to obtain the catalyst of the present invention.

Example 5

Characterization of the Catalysts

The comparative catalysts (Examples 1) and the catalyst of the present invention (Examples 3 and 4) were analyzed using X-ray Diffraction methods (XRD). The XRD data were obtained by using Philips X'pert Pro. X-ray source: Cu K alpha, voltage 40 KV, current 40 mA. Scan parameters are: range 10-90 degrees, step size 0.02 degrees, time per step 1.5 sec. The existing catalyst phases are listed in Table 1.

TABLE 1

| Catalyst | SiO$_2$ (α-cristobalite) | Na$_2$WO$_4$ | MnMn$_6$SiO$_{12}$ (Braunite) | MnWO$_4$ |
|---|---|---|---|---|
| Example 1 | x | x | x | |
| Example 3 | x | | | x |
| Example 4 | x | | | x |

From the data in Table 1, substantial differences between the catalysts of the present invention (Examples 3 and 4) and the comparative catalyst of Example 1 were observed. All phases exhibited a $SiO_2$, α-cristobalite phase. The catalysts of the present invention, Examples 3 and 4, exhibited a main $MnWO_4$ phase and no $Na_2WO_4$ and $MnMn_6SiO_{12}$ phases. The comparative Example 1 exhibited the main phases of $Na_2WO_4$ and $MnMn_6SiO_{12}$. Thus, the catalysts of the present invention are different from the comparative catalyst.

Example 6

Catalyst Performance

The comparative catalyst and the catalysts of the present invention were tested in an oxidation of methane reaction to determine their activity. All catalysts were tested in a 4 mm ID quartz reactor. The catalyst reactor was filled with the catalytic material (100 mg) with particle size of 35-50 mesh. The reactor was heated to the required temperature and reactant gas ($CH_4:O_2$ ratio 7.4) was fed into the reactor at a flow rate of 33.3 sccm. Table 2 shows the catalytic performance at 800° C. for the OCM reaction for the Comparative catalysts from Example 1 and the catalyst of the present invention, Examples 3 and 4.

TABLE 2

| Catalyst | $CH_4$ conv. (%) | $O_2$ Conv. (%) | $C_2$+ Sel. (%) | Conv. + Sel. (%) |
| --- | --- | --- | --- | --- |
| Example 1 | 18.1 | 98.2 | 78.8 | 96.3 |
| Example 3 | 18.0 | 98.6 | 79.0 | 97.0 |
| Example 4 | 20.3 | 100.0 | 82.4 | 102.7 |

From the data, it was determined that the powdered (microstructured) $MnWO_4$ with sodium in the silica support material exhibited the same selectivity and conversion vales as the conventionally made catalyst. The nanostructured $MnWO_4$ catalyst of Example 4 demonstrated higher selectivity and conversion as compared to Examples 1 and 3. Methane conversion plus selectivity can be used as an indicator of catalyst performance and most known OCM catalysts have a conversion plus selectivity value of less than 100. The catalyst of the present invention (Example 4) had a methane conversion plus selectivity value of 102, which is greater than the conventional values.

The invention claimed is:

1. A supported $MnWO_4$ catalyst comprising:
    a silicon dioxide ($SiO_2$) support material comprising sodium (Na); and
    manganese tungsten tetroxide ($MnWO_4$) in contact with the $SiO_2$ support material.
2. The supported catalyst of claim 1, wherein the molar ratio of Mn to W is 1:1.
3. The catalyst of claim 1, wherein the supported catalyst comprises a $MnWO_4$ crystal phase.
4. The supported catalyst of claim 1, wherein the Mn and W are chemically bound together or are in close proximity with one another.
5. The supported catalyst of claim 1, wherein the $MnWO_4$ is $MnWO_4$ nanostructures, and wherein the nanostructures have at least one dimension of 1 nm to 1000 nm.
6. The supported catalyst of claim 5, wherein the $MnWO_4$ nanostructures are nanowires, nanoparticles, nanorods, nanotubes, or nanocubes, or a combination thereof.
7. The supported catalyst of claim 6, wherein the $MnWO_4$ nanostructures are nanorods having a diameter of 10 nm to 50 nm and/or a length of 150 nm to 250 nm.
8. The supported catalyst of claim 1, wherein the supported catalyst is devoid of a $Na_2WO_4$ crystal phase and devoid of a $MnMn_6SiO_{12}$ crystal phase.
9. The supported catalyst of claim 1, wherein the catalyst is capable of catalyzing an oxidative coupling of methane reaction.
10. The supported catalyst of claim 1, wherein the $MnWO_4$ nanostructures are grafted to the surface of the support material.
11. A method for preparing the supported $MnWO_4$ catalyst of claim 1, the method comprising:
    (a) obtaining an aqueous mixture comprising manganese tungsten oxide ($MnWO_4$) or manganese tungsten oxide ($MnWO_4$) nanostructures and a silica support material comprising sodium;
    (b) drying the mixture to obtain a crystalline material; and
    (c) calcining the crystalline material to obtain a $MnWO_4$ supported catalyst.
12. The method of claim 11, wherein the silica support material in step (a) is obtained by:
    (i) obtaining an aqueous mixture of a sodium source and silica sol;
    (ii) drying the mixture to obtain a crystalline material; and
    (iii) calcining the crystalline material to obtain the silica support material.
13. The method of claim 11, wherein the $MnWO_4$ nanostructures are nanowires, nanoparticles, nanorods, nanotubes, nanocubes, or a combination thereof.
14. The method of claim 13, wherein the nanostructures are nanorods.
15. The method of claim 11, wherein the sodium source is NaCl, $NaNO_3$, $Na_2CO_3$, or $Na_2O$, or a mixture thereof.
16. The method of claim 11, wherein drying step (b) comprises subjecting the mixture to a temperature of 110° C. to 130° C. for 1 hours to 15 hours, preferably 125° C.
17. The method of claim 11, wherein calcining step (c) comprises subjecting the crystalline material to a temperature of 350° C. to 800° C. in the presence of air.
18. The method of claim 11, wherein the $MnWO_4$ supported catalyst has a $MnWO_4$ phase in the crystal structure.
19. A method for producing $C_2$+ hydrocarbons from an oxidative coupling of methane reaction, the method comprising contacting a reactant feed that includes methane ($CH_4$) and oxygen ($O_2$) with the catalysts of claim 1 under reaction conditions sufficient to produce a product stream comprising $C_2$+ hydrocarbons.
20. The method of claim 19, wherein the sum of the $CH_4$ conversion percentage and the $C_2$+ hydrocarbon selectivity percentage is greater than 100.

* * * * *